(12) United States Patent
Berger et al.

(10) Patent No.: US 9,980,883 B2
(45) Date of Patent: May 29, 2018

(54) TEMPERATURE INDICATING ENDODONTIC OBTURATION MATERIAL

(71) Applicant: DENTSPLY SIRONA Inc., York, PA (US)

(72) Inventors: Todd Berger, Owasso, OK (US); Adam Baratz, Broken Arrow, OK (US); Jaclyn Vasseur, Broken Arrow, OK (US)

( * ) Notice: Subject to any disclaimer, the term of this patent is extended or adjusted under 35 U.S.C. 154(b) by 28 days.

(21) Appl. No.: 15/092,101

(22) Filed: Apr. 6, 2016

(65) Prior Publication Data
US 2016/0296425 A1    Oct. 13, 2016

Related U.S. Application Data

(60) Provisional application No. 62/143,919, filed on Apr. 7, 2015.

(51) Int. Cl.
*A61K 6/083* (2006.01)
*A61K 6/00* (2006.01)

(52) U.S. Cl.
CPC ............ *A61K 6/0064* (2013.01); *A61K 6/007* (2013.01); *A61K 6/0038* (2013.01); *A61K 6/0058* (2013.01); *A61K 6/083* (2013.01)

(58) Field of Classification Search
USPC ............... 523/116, 117; 433/224, 228.1
See application file for complete search history.

(56) References Cited

U.S. PATENT DOCUMENTS

| | | | | |
|---|---|---|---|---|
| 1,988,483 | A | * | 1/1935 | Croakman ............... D06P 3/793 524/325 |
| 4,483,679 | A | | 11/1984 | Fujisawa et al. |
| 2006/0194895 | A1 | | 8/2006 | Loveridge et al. |
| 2008/0085948 | A1 | * | 4/2008 | Primus ................. A61K 6/0094 523/116 |
| 2014/0004071 | A1 | | 1/2014 | Brown |

FOREIGN PATENT DOCUMENTS

| | | |
|---|---|---|
| JP | 2000210305 A | 8/2000 |
| WO | 9927895 | 6/1999 |
| WO | 2008008184 A2 | 1/2008 |
| WO | 2014182570 A1 | 11/2014 |

OTHER PUBLICATIONS

International Search Report and Written Opinion of PCT/US2016/026179 dated May 19, 2016.
International Preliminary Report on Patentability of PCT/US2016/026179 dated Oct. 10, 2017.

* cited by examiner

*Primary Examiner* — Tae H Yoon
(74) *Attorney, Agent, or Firm* — David A. Zdurne; Douglas J. Hura; Leana Levin

(57) ABSTRACT

A gutta-percha composition for filling a tooth root canal includes a temperature indicating component, such that the user has a visual indication that the material is ready for placement in the prepared canal. The material may include a thermochromatic dye, bismuth oxide or the like, in an otherwise conventional obturation material.

6 Claims, No Drawings

US 9,980,883 B2

TEMPERATURE INDICATING ENDODONTIC OBTURATION MATERIAL

RELATED APPLICATION

This application is a non-provisional of Provisional U.S. Application No. 62/143,919 filed on Apr. 7, 2015.

TECHNICAL FIELD

The present invention relates to endodontic obturation materials. More particularly, the invention relates to obturation materials that show a color change as an indication of temperature change.

BACKGROUND OF THE INVENTION

Gutta-percha (*Palaquium*) is a genus of tropical trees native to Southeast Asia and northern Australasia, from Taiwan south to the Malay Peninsula and east to the Solomon Islands. The same term is used to refer to inelastic natural latex produced from the sap of these trees, particularly from the species *Palaquium gutta*. Chemically, gutta-percha is a polyterpene, a polymer of isoprene, or polyisoprene, specifically (trans-1, 4-polyisoprene). Examples of known gutta-percha compositions and certain uses thereof are disclosed for example in published patent application WO2014182570A1, which is hereby incorporated by reference for such disclosure.

The bio inertness of gutta-percha makes it suitable for use within the human body. It is used in a variety of dental applications. In the 1900's this material was used to fill cavities. In the early 1900's the material was used in root canal therapy. Gutta-percha remained a staple well into the 20$^{th}$ century, when it was gradually replaced by alternative materials. A similar, cheaper natural material called balata is often used in gutta-percha's place. The two materials are almost identical, and balata is sometimes called gutta-ballata. For simplicity, all such materials will be encompassed by the term "gutta-percha" for purposes of this disclosure.

A material used to obturate or fill the empty space inside the root of a tooth after it has undergone root canal therapy, is often called "synthetic" in the dental arts. Synthetic became more readily available as the demand increased and the availability of natural material decreased. Its physical and chemical properties, including but not limited to its inertness and biocompatibility, melting point, and malleability, make it an important material used in endodontics. Synthetic is also encompassed by the term "gutta-percha" herein, again for simplicity sake. It will be understood that any conventional root canal obturation material is within the scope of the term "gutta-percha" herein.

Gutta-percha and more particularly, trans-1,4, polyisoprene was originally used as a cold material to fill the root canal. The material was rolled into a cone shaped point to fill the canal. The use of sealant was added to fill the voids around the points. Eventually the material was heated. The heated (melted) gutta-percha flowed to fill the voids and cavities within the canal. Heating was preferred because it allowed for a three dimensional fill, substantially absent of voids. The use of heated gutta-percha introduced new adjustable parameters, such as temperature, flow rate and tackiness.

When filling a root canal, heated gutta-percha is normally delivered by one of two methods. It can be placed with an electronic delivery device or placed on an endodontic carrier. Both methods deliver it hot into the canal, and both methods conventionally require compaction either with a metal plugger or the endodontic carrier. Further, these methods require the material to be within a temperature range ideal for the compaction.

Currently, the dental or endodontic clinician relies on the appearance of the surface or the feel when touched with a gloved finger to determine if the gutta-percha is heated to the correct temperature for placement. When looking at the gutta-percha, the clinician can tell if the material has been heated, (the material often becomes more "plump") but not if it is currently the right temperature. If the material is too hot, it may not place well and the canal will not be properly obturated. Similarly, if the material is too cold it will not flow or place properly. The clinician will try to place the material into the canal and find that it will not fill the voids or not completely fill the canal.

The present invention overcomes these difficulties, giving the clinician a precise real time temperature indicator which allows for ease of placement and will substantially take the temperature estimate out of the procedure. This will give assurance that the material will place properly and fill the endodontically prepared root canal as needed.

DISCLOSURE OF THE INVENTION

According to the invention, a gutta-percha composition for filling a tooth root canal includes a temperature indicating component. The component can be for example, a Leuco dye. The gutta-percha composition may include a trans 1-4, polyisoprene, wherein the temperature indicating additive is present in an amount of about 1% to about 70% by weight of the gutta-percha composition. The gutta-percha composition may also include a radiopacifier.

In another embodiment of the invention, a composition for filling a tooth root canal includes two different temperature indicating ingredients which indicate different temperature ranges. The two different temperature indicating ingredients may be for example, a Leuco dye and bismuth oxide.

In a further embodiment of the invention, a temperature indicating ingredient may be a wax which blooms to the surface and when warm, producing a glossy surface to the gutta-percha. Such a material may be used with a second temperature indicating ingredient such as a dye or bismuth oxide that indicates a different temperature.

PREFERRED EMBODIMENTS FOR CARRYING OUT THE INVENTION

According to the present invention, an endodontic obturation material is provided that indicates the current temperature of the material by a relative color indication. The Temperature Indicating material of the invention was developed to be used with obturator devices because it was observed that clinicians often touch the gutta-percha with their finger to make sure the gutta-percha was hot and soft. The desire was to provide proof the oven or other conventional heating method or device properly heated the gutta-percha and to avoid any unnecessary contamination by foreign material or bacteria of the gutta-percha prior to inserting it into the prepared root canal.

Temperature indicating gutta-percha is a unique formulation with the same physical and thermal properties of otherwise conventional obturation materials such as Thermafil gutta-percha available from DENTSPLY SIRONA of York, Pa. These gutta-percha materials have good tack and flow once the alpha phase process has been completed. The alpha phase process is a long term (8 to 12 hour) bake at elevated temperature (115 to 160° C.). Many standard gutta-percha formulations separate, even producing a brown oil at these temperatures. The remaining gutta-percha itself becomes brittle.

According to the present invention, gutta-percha survives the alpha phase process without separating or producing the brown oil and the gutta-percha does not become brittle. The thermal properties of the inventive gutta-percha materials after the alpha phase process are changed. The melt flow increases dramatically (≤5 to >50 g/10 min at 180° C.). The change to the conventional materials includes a certain ratio of processing aids which are shown in the FORMULATION section below.

Another inventive characteristic of the present materials is a temperature indicating property. The following are examples of these gutta-percha formulations.

Example 1—replace the majority of the radiopacifier used in a conventional gutta-percha material with bismuth oxide. Standard gutta-percha uses zinc oxide and barium sulfate to generate a radiopacity of 6 mmAl (mm of aluminum). The bismuth oxide is known to be a good radiopacifier however it is also an indicator of temperature. At low temperatures it is a mild yellow color. At elevated temperature it is a bright yellow color.

Example 2—replace the conventional colorant with thermochromic dyes. A red colorant is often used in standard gutta-percha to give it a standard and well-known pink color. Thermochromic dyes used in the present invention are designed to change from a color to clear at a specified temperature. They preferably fall into two temperature ranges; 40 to 50° C. and 60 to 70° C. These temperature ranges are ideal for gutta-percha obturation materials. Gutta-percha begins to melt at about 42° C. The 40 to 50° C. dye indicates the gutta-percha has melted and the 60 to 70° C. dye indicates the gutta-percha is much hotter than needed to melt.

Color:

EXAMPLE 1

Bismuth Oxide

| Ingredients | Weight % |
|---|---|
| Trans-1,4-polyisoprene | 25 |
| Zinc Oxide | 28.5 |
| Bismuth Oxide | 36 |
| Antioxidant | 1 |
| Antiozidant | 2.5 |
| Processing Aid | 1.5 |
| White Colorant | 5 |
| Red Colorant | 0.5 |
| Total | 100 |

EXAMPLE 2

Thermochromic Dye

| Ingredients | Weight % |
|---|---|
| Trans-1,4-polyisoprene | 25 |
| Zinc Oxide | 51 |
| Barium Sulfate | 10 |
| Antioxidant | 1 |
| Antiozidant | 2.5 |
| Processing Aid | 1.5 |
| White Colorant | 5 |
| TP060B Blue | 2 |
| TP047R Red | 2 |
| Total | 100 |

Another exemplary formulation is shown below in Table 1.

TABLE 1

Example Formulation

| Ingredient | Weight % |
|---|---|
| Trans-1,4-polyisoprene | 24.2 |
| Zinc Oxide | 70.7 |
| QCR TP047K (47C Black Thermo) | 4.9 |
| Total | 100 |

The trans-14-polyisoprene is first baked in a 130° C. oven for 7.5 hours. The baked polyisoprene was then allowed to cool for at least 24 hours. The polyisoprene was placed into a 71° C. oven for a half-hour, and then the polyisoprene was formed into a ball and placed back into the oven. After a half-hour, the polyisoprene was removed from the oven and placed onto a heated two-roll mill that was set to 60° C. The Zinc Oxide was then added to the polyisoprene on the mill a little at a time. Once all of the Zinc Oxide was incorporated, the material was cross-cut at least 5 times. The QCR TP047K (47C Black Thermo) was then added in the same way as the Zinc Oxide. Once all of it was added, the formulation was again cross-cut at least 5 times in order to fully mix in the colorant. The formulation was then pigged at least 3 times, and then removed from the mill, laid down on a flat surface covered with release liner, and allowed to cool for at least 24 hours.

The material produced in Table 1 was then converted into pellets with a nominal diameter of 1 mm and 14 mm length. The pellets were then applied to carriers. This process can be used to produce finished obturators.

The pellets produced in the above example can also be loaded into cartridges and used in obturation devices such as the Calamus brand obturation devices available from DENTSPLY International of York, Pa.

Table 1 presents an example of the present invention. Table 2 presents several examples with a similar functionality.

TABLE 2

Several Example Formulations

| Ingredient | Example 1 | Example 2 | Example 3 | Example 4 |
|---|---|---|---|---|
| Trans-1,4-polyisoprene | 25% | 25% | 25% | 25% |
| Zinc Oxide | 70% | 65% | | 65% |
| Leuco Dye 47° C. | 5% | 5% | | |
| Leuco Dye 69° C. | | 5% | | |
| Bismuth Oxide | | | 75% | |
| Wax | | | | 10% |
| Total | 100% | 100% | 100% | 100% |

Example 1 has already been explained. Example 2 has the unique property to identify when the material is not only warm so that it is soft but also when it is too hot and may be too runny. The material is a bas color about 60° C. Between 47 and 69° C. it is the color of the Leuco Dye 69° C. And the gutta-percha is the optimum temperature with the optimum properties. As the material cools to below 47° C. the color changes to a blend of Leuco Dye 47° C. and Leuco Dye 69° C. (red and blue=purple).

Example 3 has been explained that bismuth oxide will also indicate a temperature change and doubles as a radiopacifier.

Example 4 indicates the gutta-percha is heated by the blooming wax melting. This would provide a glassy look to the surface.

It is therefore evident that an endodontic obturation material having desirable and inventive characteristics has been provided by the present invention. The invention has been characterized herein by way of examples and discussion for exemplary purposes only.

The invention claimed is:

1. A composition for filling a tooth root canal comprising:
   a gutta-percha component;
   a first temperature indicating component; and
   a second temperature indicating component;
   wherein said first and said second temperature indicating components provide temperature indication at at least two different temperature ranges from each other; and
   wherein said first temperature indicating component changes color when it reaches a temperature of from about 40 to about 50 degrees C., and said second temperature indicating component changes color when it reaches a temperature of from about 60 to about 70 degrees C.

2. A composition as in claim 1, wherein said gutta-percha component includes 1,4-polyisoprene.

3. A composition as in claim 1 wherein said thermochromic dye is present in an amount of from about 1 to about 70 percent by weight of said composition.

4. A composition as in claim 1, wherein said second temperature indicating component is bismuth oxide.

5. A composition for filling a tooth root canal comprising:
   a gutta-percha component, wherein said gutta-percha component includes 1,4-polyisoprene;
   a thermochromic dye being present in an amount of from about 1 to about 70 percent by weight of said composition; and
   a radiopacifier;
   wherein said thermochromic dye changes color when it reaches a temperature of from about 40 to about 50 degrees C. or from about 60 to about 70 degrees C.

6. A composition as in claim 1, further comprising a radiopacifier.

* * * * *